United States Patent [19]

Sauer

[11] Patent Number: 4,959,317
[45] Date of Patent: Sep. 25, 1990

[54] SITE-SPECIFIC RECOMBINATION OF DNA IN EUKARYOTIC CELLS

[75] Inventor: Brian L. Sauer, Greenville, Del.

[73] Assignee: E. I. Du Pont de Nemours and Company, Wilmington, Del.

[21] Appl. No.: 43,795

[22] Filed: Apr. 29, 1987

Related U.S. Application Data

[63] Continuation-in-part of Ser. No. 784,951, Oct. 7, 1985.

[51] Int. Cl.$^5$ .................. C12P 21/00; C12P 19/34; C12N 15/00; C12N 5/00
[52] U.S. Cl. ................ 435/172.3; 435/240.1; 435/240.2; 435/69.1; 435/91; 435/254; 435/255; 435/256; 435/320
[58] Field of Search ............ 435/68, 70, 172.1, 172.3, 435/253, 317, 320, 256, 254, 255, 91, 240.2; 530/360; 536/27; 935/28, 34, 69, 37

[56] References Cited

U.S. PATENT DOCUMENTS 4,626,505 12/1986 Falco ........................ 435/172.3
4,673,640 6/1987 Backman .................. 435/172.3

OTHER PUBLICATIONS

Abremski et al., Cell, vol. 32 (1983), 1301–1311.
Backman et al., Biotechnology (1984), 1045–1049.
Brent et al., Nature, vol. 312 (1984), 612–614.
Langeveld et al., Mol. Gen. Genet. (1985), 396–400.
Okayama et al., Mol. and Cell. Biol., vol 5 (1985), 1136–1142.
Barnes et al., Proc. Natl. Acad. Sci. 82: 1354–1358 (1985).

Primary Examiner—Robin L. Teskin
Attorney, Agent, or Firm—William H. Hamby

[57] ABSTRACT

A method for producing site-specific recombination of DNA in eukaryotic cells at regions designated lox sites is disclosed.

40 Claims, 9 Drawing Sheets

F I G. 3A
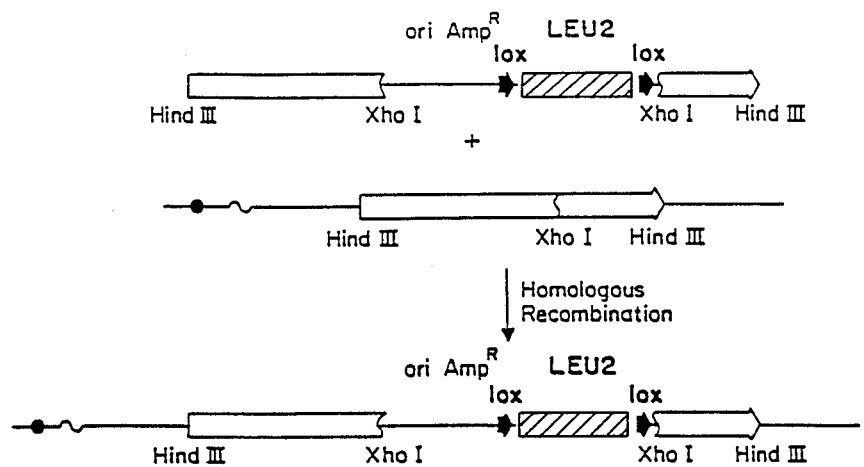
F I G. 3B
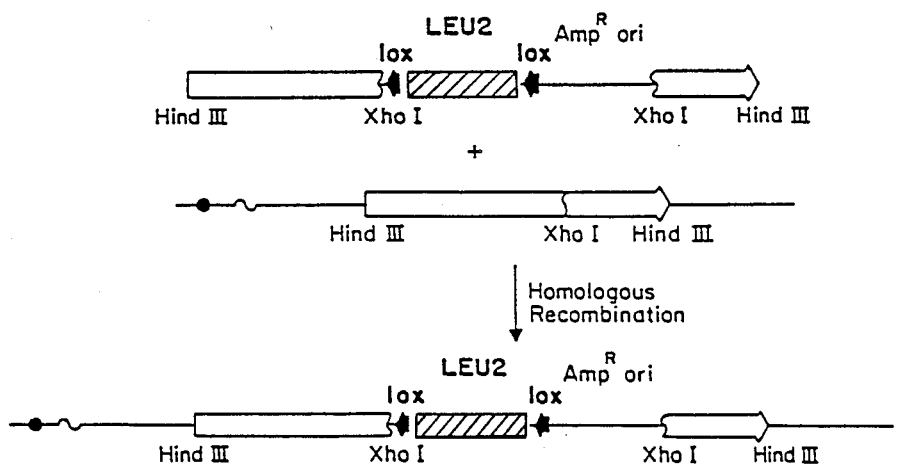

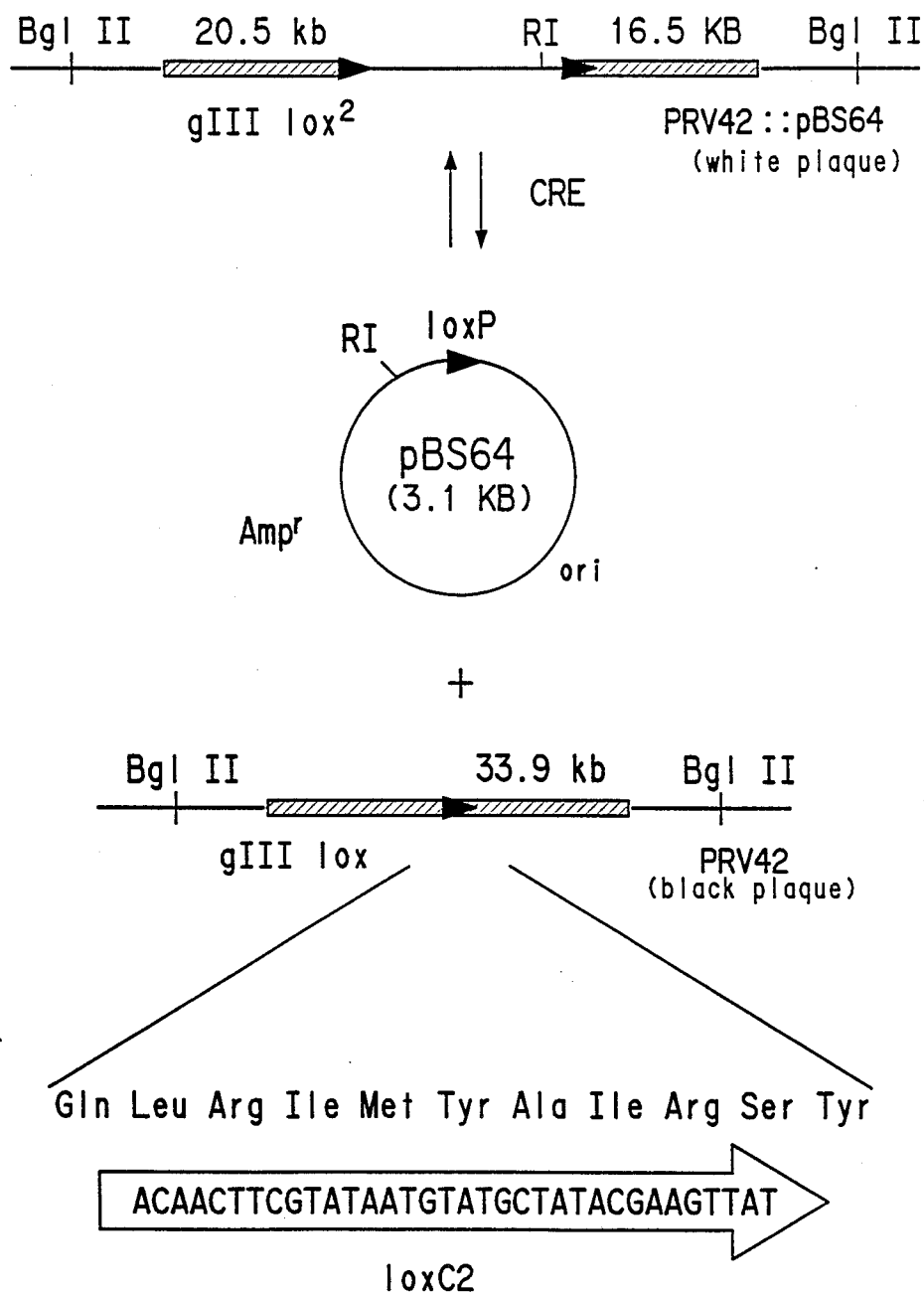

SITE-SPECIFIC RECOMBINATION OF DNA IN EUKARYOTIC CELLS

CROSS-REFERENCE TO RELATED APPLICATIONS

This application is a continuation-in-part of copending U.S. Ser. No. 784,951 filed Oct. 7, 1985 and entitled "Site-Specific Recombination of DNA in Yeast".

BACKGROUND OF THE INVENTION

1. Field of the Invention

This invention relates to a method for producing site-specific recombination of DNA in eukaryotic cells.

2. Background of the Invention

Many eukaryotic cells, including yeast, are promising hosts for commercial applications of genetic engineering. A method for producing site-specific recombination of DNA in eukaryotic cells would enhance the commercial potential of these cells as hosts for genetically engineered products. In addition, methods for producing site-specific recombination of DNA in eukayotic cells, such as mammalian cells, are of interest to the medical field.

Abremski et al., *Cell*, 32: 1301—1311 (1983) disclose a site-specific recombination system of bacteriophage P1. The system consists of a recombination site designated loxP and a recombinase designated Cre. The authors show that recombination between loxP sites on supercoiled, nicked-circle or linear DNA occurs in the presence of Cre.

Brent et al., *Nature*, 312: 612–615 (1984) disclose that a bacterial repressor protein or a yeast transcriptional terminator can block upstream activation of a yeast gene. Disclosed experiments are said to provide genetic evidence that a bacterial repressor protein manufactured in the yeast cytoplasm can enter the yeast nucleus, recognize its operator and repress gene transcription from a yeast promoter.

Barnes et al., *Proc. Natl. Acad. Sci.* 82: 1354-1358 (1985) disclose that the bacterial restriction enzyme Eco RI is able to enter and function within the nucleus of *Saccharomyces cerivisiae* when the procaryotic protein is synthesized in vivo.

Backman et al., *Bio/Technology* (December, 1984) disclose a site-specific recombination system of the bacteriophage lambda. The system catalyzes recombination between two different sites in DNA, designated attP and attB, to yield two other different sites, designated attR and attL, or vice versa. Recombination occurs only in the presence of certain *E. coli* proteins and the Int protein of bacteriophage lambda and can be used to regulate gene expression of *E. coli* Langeveld et al., *Mol. Gen. Genet.*, 199:396–400 (1985) disclose expression of an *E. coli* phr gene in yeast *Saccharomyces cerevisiae*.

SUMMARY OF THE INVENTION

The present invention provides a method for producing site-specific recombination of DNA in eukaryotic cells. The method comprises:

(a) introducing into the cells a first DNA sequence comprising a first lox site and a second DNA sequence comprising a second lox site, and (b) contacting the lox sites with Cre, thereby producing the site specific recombination.

In a preferred embodiment, a third DNA sequence comprising a cre gene is also introduced into the cells.

Most preferably, the third DNA sequence further comprises a regulatory nucleotide sequence and expression of the cre gene is produced by activating the regulatory nucleotide sequence. In another preferred embodiment, the first and second DNA sequences are introduced into the DNA connected by a pre-selected DNA segment. In one embodiment, the eukaryotic cell is yeast.

BRIEF DESCRIPTION OF THE DRAWINGS

FIG. 3 represents the modification of chromosome 7 of yeast strain DBY931 after homologous recombination with pBS42 (panel A) or pBS43 (panel B). The lox sites are indicated by ▶. The centromere is indicated by ●.

FIG. 9 shows schematic representation of the predicted cre-mediated recombination event of PRV42::pBS64. Cre causes the recombination of the lox sites in the disrupted gIII gene of PRV42::pBS64 to generate a small circular molecule and a viral genome (PRV42) which contains a reconstructed gIII gene capable of expressing the M1 epitope. Reconstruction of the gene, via site specific recombination, can be detected by the black plaque assay. The shaded boxes represent the PRV gIII gene; the arrow represents the 34 bp lox site. The DNA sequence encased by the arrow in the lower part of the figure is the sequence of loxC2 which is present in PRV42.

DETAILED DESCRIPTION OF THE INVENTION

Figure 1:
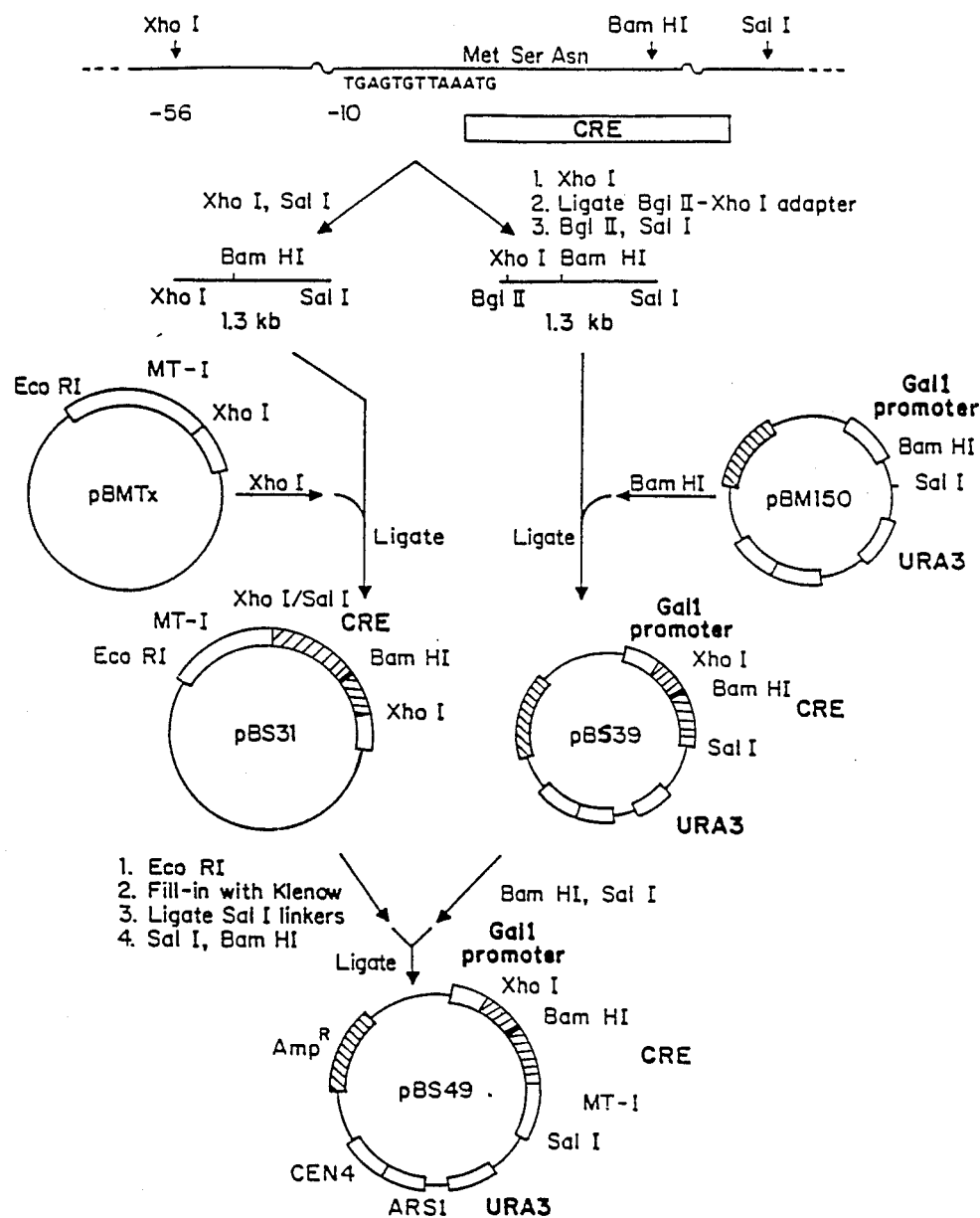
FIG. 1 represents the construction of plasmids pBS39 and pBS49, containing the GAL1 promoter and the cre gene.

The present invention provides a method for producing site-specific recombination of DNA in eukaryotic cells. DNA sequences comprising first and second lox sites are introduced into eukaryotic cells and contacted with Cre, thereby producing recombination at the lox sites. It has been found that the location and orientation of the lox sites determines the nature of the recombination.

As used herein, the expression "site-specific recombination" is intended to include the following three events:
1. deletion of a pre-selected DNA segment flanked by lox sites,
2. inversion of the nucleotide sequence of a preselected DNA segment flanked by lox sites, and
3. reciprocal exchange of DNA segments proximate to lox sites located on different DNA molecules.

It is to be understood that this reciprocal exchange of DNA segments can result in an integration event if one or both of the DNA molecules are circular. "DNA segment" refers to a linear fragment of single- or double-stranded deoxyribonucleic acid (DNA), which can be derived from any source. The expression "DNA in eukaryotic cells" includes all DNA present in eukaryotic cells. The expression "DNA in yeast" includes all DNA present in yeast cells. As used herein, a "gene" is intended to mean a DNA segment which is normally regarded as a gene by those skilled in the art. The expression "regulatory molecule" refers to a polymer of ribonucleic acid (RNA) or a polypeptide which is capable of enhancing or inhibiting expression of a gene.

"Regulatory nucleotide sequence", as used herein, refers to a nucleotide sequence located proximate to a gene whose transcription is controlled by the regulatory nucleotide sequence in conjunction with the gene expression apparatus of the cell. Generally, the regulatory nucleotide sequence is located 5' to the gene. The expression "nucleotide sequence" refers to a polymer of DNA or RNA, which can be single- or double-stranded, optionally containing synthetic, non-natural, or altered nucleotides capable of incorporation into DNA or RNA polymers. As used herein, a "regulatory nucleotide sequence" can include a promoter region, as that term is conventionally employed by those skilled in the art. A promoter region can include an association region recognized by an RNA polymerase, one or more regions which control the effectiveness of transcription initiation in response to physiological conditions, and a transcription initiation sequence. "Gene product" refers to a polypeptide resulting from transcription, translation, and, optionally, post-translational processing of a selected DNA segment.

In the present invention first and second DNA sequences comprising a first lox site and a second lox site, respectively, are introduced into eukaryotic cells. As used herein the expression "lox site" means a nucleotide sequence at which the gene product of the cre gene, referred to herein as Cre, can catalyze a site-specific recombination. LoxP site is a 34 base pair nucleotide sequence which can be isolated from bacteriophage P1 by methods known in the art. One method for isolating a LoxP site from bacteriophage P1 is disclosed by Hoess et al., *Proc. Natl. Acad. Sci. USA*, 79:3398 (1982). The LoxP site consists of two 13 base pair inverted repeats separated by an 8 base pair spacer region. The nucleotide sequences of the insert repeats and the spacer region are as follows.

ATAACTTCGTATA ATGTATGC
TATACGAAGTTAT

*E. coli* DH5 Δlac and yeast strain BSY23 transformed with plasmid pBS44 carrying two loxP sites connected with a LEU2 gene have been deposited with the ATCC and bear deposit accession numbers ATCC 53254 and ATCC 20773, respectively. The lox sites can be isolated from plasmid pBS44 with restriction enzymes Eco RI and Sal I, or Xho I and Bam I. In addition, a preselected DNA segment can be inserted into pBS44 at either the Sal I or Bam I restriction enzyme sites by techniques known in the art. Other suitable lox sites include LoxB, LoxL and LoxR sites which are nucleotide sequences isolated from *E. coli*. These sequences are disclosed and described by Hoess et al., *Proc. Natl. Acad. Sci USA*, 79:3398 (1982). Preferably, the lox site is LoxP or LoxC2. Lox sites can also be produced by a variety of synthetic techniques which are known in the art. For example, synthetic techniques for producing lox sites are disclosed by Ito et al., *Nuc. Acid Res.*, 10:1755 (1982) and Ogilvie et al., *Science*, 214:270 (1981), the disclosures of which are incorporated herein by reference.

Methods for introducing a DNA sequence into eukaryotic cells are known in the art. These methods typically include the use of a DNA vector to introduce the sequence into the DNA of a single or limited number of eukaryotic cells and then growing such cell or cells to generate a suitable population of cells. As used herein, the term "vector" includes plasmids and viruses. Preferably, the DNA sequences are introduced by a plasmid capable of transforming a selected eukaryotic cell while carrying a DNA sequence. The particular vector which is employed to introduce the DNA sequence into a selected eukaryotic cell is not critical. In a preferred embodiment, DNA sequences are introduced into mammalian cells according to the CaPO4 transfer procedure described by Graham and van den Eb, *Virology*, 52:456-467 (1973).

In the present method, the lox sites are contacted with Cre, thereby producing the site specific a first DNA sequence comprising a cre gene is introduced into eukayotic cells. In one embodiment, Cre is introduced into the cells directly by microinjection In a preferred embodiment, the cre gene is introduced into the eukaryoic cell under the control of a regulatory nucleotide sequence. Suitable regulatory nucleotide sequences are known in the art. The regulatory nucleotide sequence which is employed with a selected eukaryotic cell is not critical to the method of the invention. A partial list of suitable regulatory nucleotide sequences includes the long terminal repeat of Moloney sarcoma virus described by Blochlinger and Diggelmann, *Mol. Cell Bio.*, 4:2929-2931 (1984); the mouse metallothionein-I promoter described by Pavlakis and Hamer, *Proc. Natl. Acad. Sci USA*, 80:397-401 (1983); the long terminal repeat of Rous sarcoma virus described by Gorman et al., *Proc. Natl. Acad. Sci USA*, 79:6777-6781 (1982); and the early region promoter of SV40 described by Southern and Berg, *J. Mol. Appl. Genet.*, 1:327-341 (1982). The disclosures of these references are incorporated herein by reference.

In an embodiment wherein the eukaryotic cells are yeast, suitable regulatory nucleotide sequences include GAL1, GAL10, ADH1, CYC1, and TRP5 promoters.

GAL1 and GAL10 promoters are present on plasmid pBM150 which is described by Johnston and Davis, *Molec. Cell. Biol.*, 4:1440 (1984). The ADH1 promoter, also called ADC1, is present on plasmid pAAH5 which is described by Ammer, *Methods Enzymol.*, 101:192 (1983). The CYC1 promoter is described by Stiles et al., *Cell*, 25:277 (1981). The TRP5 promoter is described by Zalkin and Yanofsky, *J. Biol. Chem.*, 257:1491 (1982). Preferably, the regulatory nucleotide sequence is a GAL1 promoter.

The gene product of the cre gene is a recombinase herein designated "Cre" which effects site-specific recombination of DNA at lox sites. As used herein, the expression "cre gene" means a nucleotide sequence which codes for a gene product which effects site-specific recombination of DNA in eukaryotic cells at lox sites. One cre gene can be isolated from bacteriophage P1 by methods known in the art. One method for isolating a cre gene from bacteriophage P1 is disclosed by Abremski et al., *Cell*, 32:1301–1311 (1983), the disclosure of which is incorporated herein by reference.

*E. coli* DH1 and yeast strain BSY90 transformed with plasmid pBS39 carrying a cre gene isolated from bacteriophage P1 and a GAL1 regulatory nucleotide sequence have been deposited with the American Type Culture Collection (ATCC) and bear deposit accession numbers ATCC 53255 and ATCC 20772, respectively. The cre gene can be isolated from plasmid pBS39 with restriction enzymes Xho I and Sal I as shown in FIG. 1.

In one embodiment wherein the eukaryotic cell is yeast, the first, second, and optionally, third DNA sequences are introduced into one strain of yeast. Alternatively, the DNA sequences are introduced into two different strains of yeast of opposite mating types which are subsequently mated to form a single strain having all three DNA sequences. Preferably, the plasmid contains either (1) a nucleotide sequence of DNA homologous to a resident yeast sequence to permit integration into the yeast DNA by the yeast's recombination system or (2) a nucleotide sequence of DNA which permits autonomous replication in yeast. One nucleotide sequence which permits autonomous replication in yeast is an ARS sequence described by Stinchcomb et al., *Nature*, 282:39 (1979). A partial list of plasmids capable of transforming yeast includes YIP5, YRP17 and YEP24. These plasmids are disclosed and described by Botstein and Davis, *The Molecular Biology of the Yeast Saccharomyces, Metabolism and Gene Expression* (ed. Strathern et al.), (Cold Spring Harbor Laboratory, Cold Spring Harbor, N.Y., 1982), at page 607.

Most preferably, the plasmid for introducing a DNA sequence comprising a regulatory nucleotide sequence and a cre gene is pBS39 or pBS49 and the plasmid for introducing a DNA sequence comprising a lox site is pBS44, pBS47, pBS42, pBS43 or derivatives thereof carrying a pre-selected DNA segment other than or in addition to the LEU2 gene located between the first and second lox sites. *E. coli* DH1 and DH5 Δlac transformed with plasmids pBS39 and pBS44, respectively, have been deposited with the ATCC and bear deposit accession numbers 53255 and 53254, respectively. Yeast strains BSY90 and BSY23 transformed with plasmids pBS39 and pBS44, respectively, have also been deposited with the ATCC and bear deposit accession numbers ATCC 20772 and ATCC 20773, respectively. These yeast strains are opposite mating types and can be mated to form a single strain having plasmid pBS39 and a pBS44 modified chromosome. The deposits are available to the public upon the grant of a patent to the assignee. However, it should be understood that the availability of a deposit does not constitute a license to practice the subject invention in derogation of patent rights granted by governmental action.

Since the lox site is an asymmetrical nucleotide sequence, two lox sites on the same DNA molecule can have the same or opposite orientations with respect to each other. Recombinations between lox sites in the same orientation result in a deletion of the DNA segment located between the two lox sites and a connection between the resulting ends of the original DNA molecule. The deleted DNA segment forms a circular molecule of DNA. The original DNA molecule and the resulting circular molecule each contain a single lox site. Recombination between lox sites in opposite orientations on the same DNA molecule result in an inversion of the nucleotide sequence of the DNA segment located between the two lox sites. In addition, reciprocal exchange of DNA segments proximate to lox sites located on two different DNA molecules can occur. All of these recombination events are catalyzed by the gene product of the cre gene.

In a preferred embodiment of the present invention, the first and second DNA sequences are introduced into eukaryotic cells connected by a pre-selected DNA segment. The segment can be a gene or any other sequence of deoxyribonucleotides of homologous, heterologous or synthetic origin. Preferably, the pre-selected DNA segment is a gene for a structural protein, an enzyme, or a regulatory molecule. If the first and second lox sites have the same orientation, activation of the regulatory nucleotide sequence produces a deletion of the pre-selected DNA segment. If the first and second lox sites have opposite orientation, activation of the regulatory nucleotide sequence produces an inversion of the nucleotide sequence of the pre-selected DNA segment.

UTILITY

Genes engineered into eukaryotic cells for producing a foreign protein are often placed under the control of a highly active promoter. The activity of the promoter can result in an overproduction of the protein which interferes with the growth of the engineered cell. This overproduction of the protein can make it difficult to grow the engineered cell in sufficient quantity to make protein production economically feasible. The present invention provides a method whereby engineered cells can be grown to a desired density prior to expressing the engineered gene. The engineered gene is expressed, as desired, by activating a regulatory nucleotide sequence responsible for controlling expression of the cre gene. Methods of controlling the expression of an engineered gene according to the present invention include the following:

(1) A DNA segment flanked by lox sites in the same orientation is introduced into DNA in a eukaryotic cell between a promoter and an engineered gene to render the promoter incapable of expressing the gene. A second DNA sequence comprising a regulatory nucleotide sequence and a cre gene is also introduced in the DNA. After the engineered cells are grown to a desired density, the regulatory nucleotide sequence is activated thereby effecting expression of the cre gene and producing a deletion of the DNA segment. The engineered gene would then be expressed.

(2) A gene for a regulatory molecule flanked by lox sites in the same orientation is introduced into DNA in a eukaryotic cell. The regulatory molecule inhibits expression of an engineered gene. A second DNA sequence comprising a regulatory nucleotide sequence and a cre gene is also introduced into the DNA. After the engineered cells are grown to a desired density, the regulatory nucleotide sequence is activated thereby effecting expression of the cre gene and producing a deletion of the gene for the regulatory molecule. The engineered gene would then be expressed.

(3) An engineered gene lacking a promoter and flanked by two lox sites in opposite orientations is introduced into DNA in a eukaryotic cell such that the 3' end of the gene lies adjacent to the transcription start site of a regulatory nucleotide sequence. A second DNA sequence comprising a regulatory nucleotide sequence and a cre gene is also introduced into the DNA. Since the engineered gene would be transcribed in the antisense direction, no engineered protein would be produced. After the engineered cell is grown to a desired density, the regulatory nucleotide sequence is activated thereby effecting expression of the cre gene and producing an inversion of the desired gene. The engineered gene could then be transcribed in the proper direction and expressed.

The present method is further described by the following examples wherein parts and percentages are by weight and degrees are Celsius, unless otherwise specified.

SITE SPECIFIC RECOMBINATIONS IN YEAST

Materials and Methods

Strains and Media

*E. coli* strains DH1 and DH5 ΔlacU169, or a derivative thereof, served as the *E. coli* hosts for all plasmids used in all experiments. The DH5 ΔlacU169 strain was obtained from Dr. Michael Berman, Litton Bionetics, and is a derivative of DH5, a variant of DH1 which is disclosed and described by Hanahan, *J. Mol. Biol.*, 166:557 (1983). Media used for bacterial growth are described in Maniatis et al., *Molecular Cloning: A Laboratory Manual* (Cold Spring Harbor Laboratory, N.Y., 1982).

The leu2 ura3 yeast strains DBY745 (mating type alpha) and DBY931 (mating type a) were used in all experiments. These strains are disclosed and described in Falco, Rose, and Botstein, *Genetics*, 105:843 (1983). A rich growth medium (YEPD) containing yeast extract peptone and dextrose (glucose) was used for non-selective yeast growth. A minimal growth medium (SD) containing dextrose and appropriate supplements was used for selective growth and scoring of nutritional markers. These media are described by Sherman et al., *Methods in Yeast Genetics* (Cold Spring Harbor Laboratory, N.Y., 1974). In experiments involving growth on galactose, 2% galactose was substituted for glucose. To add the selective agent sulfometuron methyl (molecular weight 364) to solid media, it was dissolved in acetone at 2 mg/mL and added to media to obtain a final concentration of 30 μg/mL immediately prior to pouring into culture dishes.

DNA Preparation and Manipulations

Plasmid DNA was prepared from *E. coli* according to (1) a rapid method substantially similar to that described by Quigley and Holmes *Anal. Biochem.* 114:193 (1981), or (2) a cesium chloride density gradient method substantially similar to that disclosed by Davis et al., *Advanced Bacterial Genetics: A Manual for Genetic Engineering* (Cold Spring Harbor Laboratory, N.Y., (1980)). Yeast DNA was prepared by a method similar to that described by Davis et al. *Methods in Enzymology*, 65: Part I (Academic Press, New York, 1980).

Selected host strains of yeast were transformed by a method similar to that of Hinnen et al., *Proc. Nat. Acad. Sci. USA* 75: 1929 (1978), except for the following modification. Recipient cells were incubated with glusulase for 2 hours at 30° in 1 M sorbitol containing 1% beta-mercaptoethanol and 0.1 M sodium citrate, pH 5.8, to form spheroplasts. *E. coli* strains were transformed according to (1) a method similar to that of Mandel and Higa, *J. Mol. Biol.* 53: 159 (1970) or (2) a method similar to that of Hanahan, *J. Mol. Biol.* 166: 557 (1983), when high efficiency was desired.

All other methods of manipulating DNA are described by Maniatis et al., *Molecular Cloning: A Laboratory Manual* (Cold Spring Harbor Laboratory, New York, 1982).

Southern Analysis and DNA Sequencing

DNA was transferred to nitrocellulose membranes from agarose gels and probed with specific labeled DNA fragments according to a method similar to that described by Southern, *J. Mol. Biol.* 98: 503 (1975), herein referred to as "Southern analysis". DNA segments were sequenced, using a dideoxynucleotide procedure similar to that of Sanger et al., *J. Mol. Biol.* 143: 161 (1980).

EXAMPLE 1

Site-Specific Deletion of LEU2 Gene in Yeast on Chromosome 7

Site-specific deletion of a LEU2 gene present in yeast Saccharomyces cerevisiae DNA was effected according to the following procedure. Yeast strains which were auxotrophic for leucine because of a leu2 gene mutation were transformed with the following plasmids—(1) pBS49 carrying a cre gene under regulatory control of a GAL1 promoter and (2) pBS42 or pBS43 carrying a functional LEU2 gene flanked by loxP sites in the same orientation. The transformed yeast strain contained a functional LEU2 gene and could grow in the absence of leucine. Activation of the GAL1 promoter with galactose effected expression of the cre gene and deletion of the LEU2 gene. The resulting yeast strain was dependent on leucine for growth.

Construction of pBS39 and pBS49

A flow chart illustrating the method used for construction of plasmids pBS39 and pBS49 is set forth in FIG. 1. Plasmid pBS7, a portion of which is shown in FIG. 1, is a derivative of plasmid pRH103 which contains the Δ6 deletion. Plasmid pBS7 differs from pRH103 in that the first DNA sequence—ATG—encountered on the cre coding strand of pBS7 starting at the Xho I site is that of an intact cre gene. Plasmid pBS7 also has a promoter which controls expression of the cre gene in *E. coli*. Plasmid pBS7 was digested with Xho I and a Bgl II-Xho I adapter (DNA sequence: TCGAGTAGATCTAC) was ligated to the digested plasmid. The resulting construct was then digested with Bgl II and Sal I. The digestion generated a cre containing fragment which was purified and then ligated to plasmid pBM150, described by Johnston and Davis, *Mol. Cell. Biol.* 4: 1440 (1984). The resulting plasmid, designated pBS39, was an autonomously replicating centromere containing yeast vector having a cre gene under control of a GAL1 promoter.

Plasmid pBS49 containing the cre gene under the control of the GAL1 promoter was derived from plasmid pBS39 according to the method shown in FIG. 1. The Xho I—Sal I fragment of pBS7 containing the cre gene was inserted into the Xho I site present in mouse metallothionein gene MT-1, described by Pavlakis and Hamer, *Proc. Nat. Acad. Sci. USA* 80:397 (1983). The resulting plasmid, designated pBS31, contained a cre gene upstream from the mouse MT-1 gene and, in particular, a 3' region of the MT-1 gene which contained a polyadenylation signal. The Eco RI site at the 3' end of the MT-1 gene was converted to a Sal I site and the resulting Sal I-Bam HI fragment was inserted into pBS39 which had been digested by Sal I and Bam HI, to form pBS49.

Plasmid pBS49 shares with pBS39 the ability to replicate autonomously in *E. coli* and yeast. Both plasmids have a cre gene under control of a GAL1 promoter In addition, pBS49 contains a mammalian polyadenylation signal, provided by the MT-1 gene, located 3' to the cre gene. The polyadenylation signal may facilitate expression of the cre gene in other eucaryotic cells. However, DNA sequences derived from MT-1 are unnecessary for cre gene expression from plasmid pBS49 in yeast, as shown below.

Construction of pBS42 and pBS43

Figure 2:
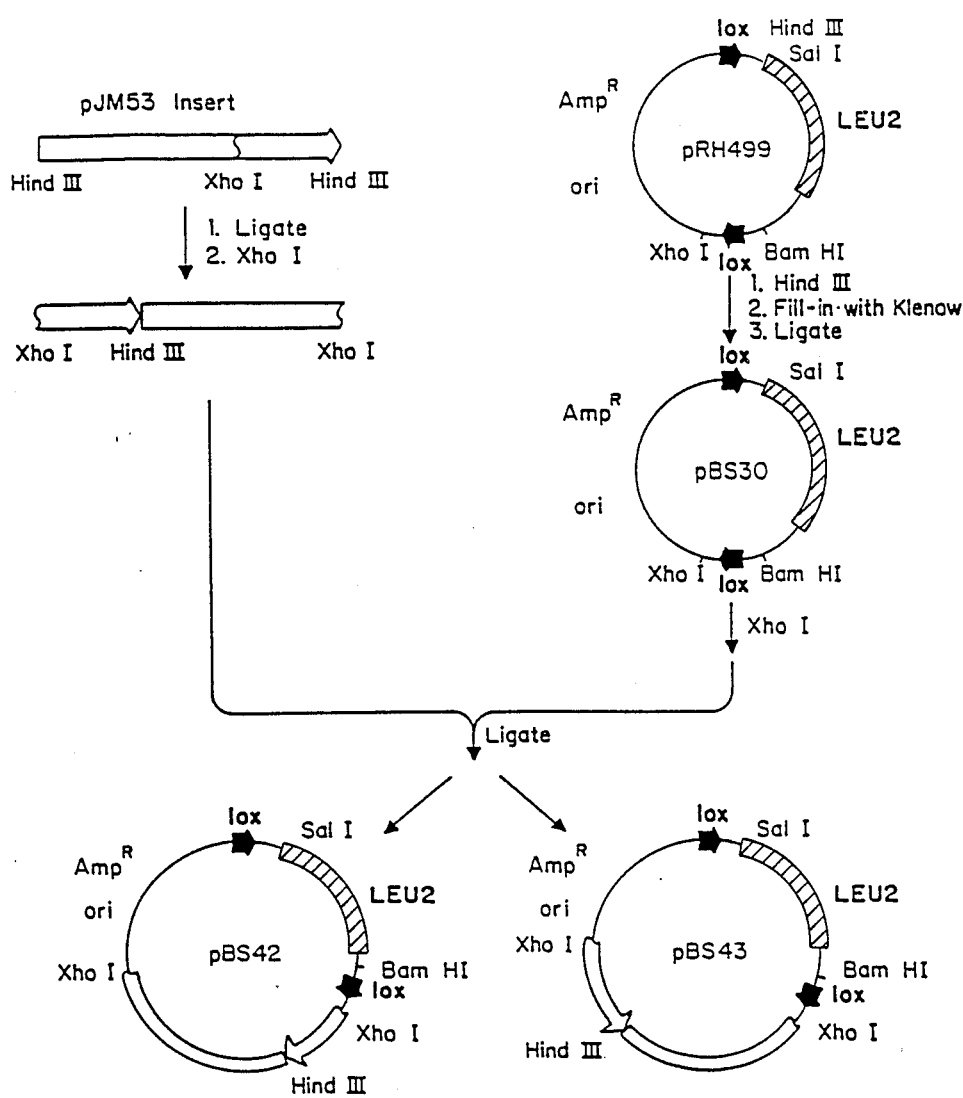
FIG. 2 represents the construction of plasmids pBS42 and pBS43, containing a functional LEU2 gene flanked by lox sites in the same orientation. The lox sites are indicated by ▶.

A flow chart illustrating the method used for construction of plasmids pBS42 and pBS43 is set forth in FIG. 2. A LEU2 gene flanked by loxP sites in the same orientation was obtained from plasmid pRH499 according to the following method. The Hind III site was removed from plasmid pRH499 to form plasmid pBS30. The 6.1 kilobase (kb) Hind III fragment of pJM53 is homologous to a region located between TRP5, a gene having a known location on chromosome 7 and required for tryptophan biosynthesis, and the LEU1 gene also having a known location on chromosome 7. This fragment was self-ligated and digested with Xho I to produce a fragment joined head to tail. The fragment was then inserted into the Xho I site of pBS30 in both orientations to produce pBS42 and pBS43. The segment of DNA from chromosome 7 present on pJM53 was included to direct the resulting plasmid to a homologous region on a yeast chromosome by the yeast's endogenous recombination system.

Transforming Yeast with pBS42 and pBS43

Plasmids pBS42 and pBS43 were linearized with Hind III and transformed into yeast strain DBY931, which contains a leu2 mutation. Yeast cells that did not require leucine for growth were selected. FIG. 3 shows that integration of these plasmids into chromosome 7 results in a leu2 gene flanked by loxP sites. The orientation of the lox sites relative to the centromere depends on whether pBS42 or pBS43 was the transforming plasmid. Integration of pBS42 generates yeast strain BSY4 having a substrate chromosome with loxP sites pointing away from the centromere of chromosome 7 as shown in FIG. 3A. Integration of pBS43 generates yeast strain BSY16 having the loxP sites pointing toward the centromere of chromosome 7 as shown in FIG. 3B.

Transforming Yeast with pBS49

The cre gene was then introduced into the yeast strains transformed with plasmids pBS42 and pBS43 according to the following procedure. Yeast strain DBY745, containing mutant genes ura3 and leu2, was transformed with plasmid pBS49 which carries a functional URA3 gene. Transformed yeast not requiring uracil for growth were selected, and designated yeast strain BSY3. Yeast strain BSY4 which contains the loxP substrate on its chromosome 7 was then mated with yeast strain BSY3 which contains plasmid pBS49 having cre gene under the control of the GAL1 promoter. This mating generated a diploid yeast strain designated BSY38. As a control, the isogenic diploid yeast strain BSY63 was constructed which differs from yeast strain BSY38 only in that it lacked plasmid pBS49. Similarly, yeast strain BSY16 was mated with yeast strain BSY3 to produce a diploid yeast strain designated BSY45 which contained both a cre gene and a modified chromosome 7. Yeast strain BSY16 was also mated with yeast strain DBY745 to produce the isogenic control strain BSY70 which lacked plasmid pBS49 and therefore the cre gene.

Effecting Production of the cre Gene Product

St. John and Davis, *Cell* 16: 443 (1979), disclose that the GAL1 promoter is inactive in cells growing on glucose but is induced to a 1000 fold greater activity in the presence of galactose. The strains shown in Table I were grown on plates containing either glucose or galactose. The resulting colonies were replicated to selective media to determine whether or not they required leucine for growth (a Leu$^{31}$ phenotype). The results are shown in Table I.

TABLE 1

| | Deletion of LEU2 Gene | | | | |
|---|---|---|---|---|---|
| Yeast Strain | Plasmid with lox sites | Plasmid with cre gene | Carbon Source | Colonies requiring leucine | Total Colonies |
| BSY38 | pBS42 | pBS49 | glu | 0 | 610 |
| BSY38 | pBS42 | pBS49 | gal | 610 | 610 |
| BSY63 | pBS42 | none | glu | 0 | 86 |
| BSY63 | pBS42 | none | gal | 0 | 80 |
| BSY45 | pBS43 | pBS49 | glu | 0 | 77 |
| BSY45 | pBS43 | pBS49 | gal | 100 | 100 |
| BSY70 | pBS43 | none | glu | 0 | 80 |
| BSY70 | pBS43 | none | gal | 0 | 100 | glu = glucose
gal = galactose

Yeast strains transformed with plasmid pBS49 carrying the cre gene, became leucine requiring (Leu$^-$) when grown on galactose but not when grown on glucose. Yeast strains lacking plasmid pBS49 showed a completely stable non-leucine requiring (Leu$^+$) phenotype. The results demonstrate that the gene product of the cre gene (1) can be expressed under the control of the GAL1 promoter, (2) is able to enter the yeast nucleus after translation in the yeast cytoplasm, and (3) does effect the recombination between two lox sites inserted into yeast DNA. Moreover, the recombination at lox sites occurs with sites having both orientations with respect to the centromere. The orientation does not affect the accessibility of the lox sites by the gene product of the cre gene.

The recombination event was shown to be efficient. A log phase culture of yeast strain BSY38 was grown with glucose as the carbon source then transferred to growth medium containing galactose. Aliquots of the yeast were removed from the medium containing galactose at the time intervals shown in FIG. 4 and plated on a non-selective medium containing leucine and glucose.

Figure 4:
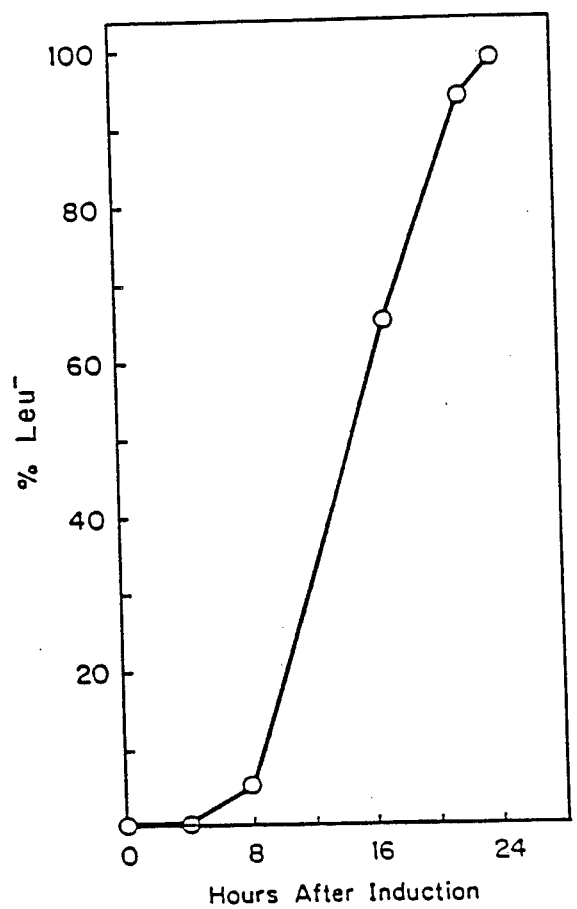
FIG. 4 shows the deletion of the LEU2 gene from yeast strain BSY38 after activation of the GAL1 promoter as described in Example 1.

The resulting colonies were assayed by replica plating to a selective medium without leucine. The resulting plates were scored after one day and the results are shown in FIG. 4. The presence of yeast requiring leucine for growth was detected 8 hours after induction with galactose. After 24 hours 98% of the initial culture had deleted the LEU2 gene as shown by this assay.

Figure 5:
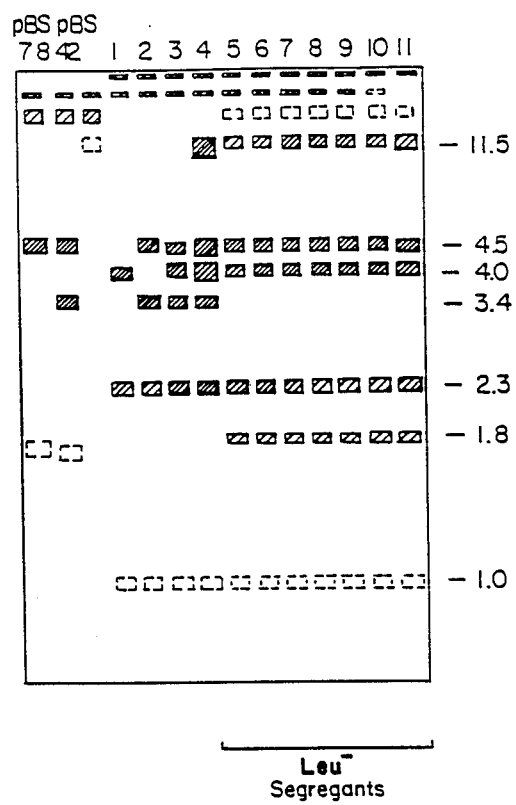
FIG. 5 shows that the deletion of the LEU2 gene occurs at the lox sites, as described in Example 1. The lox sites are indicated by ▶; Eco RI sites are indicated by ↑. The distance between Eco RI sites is indicated in kilobases (kb).
Figure 5:
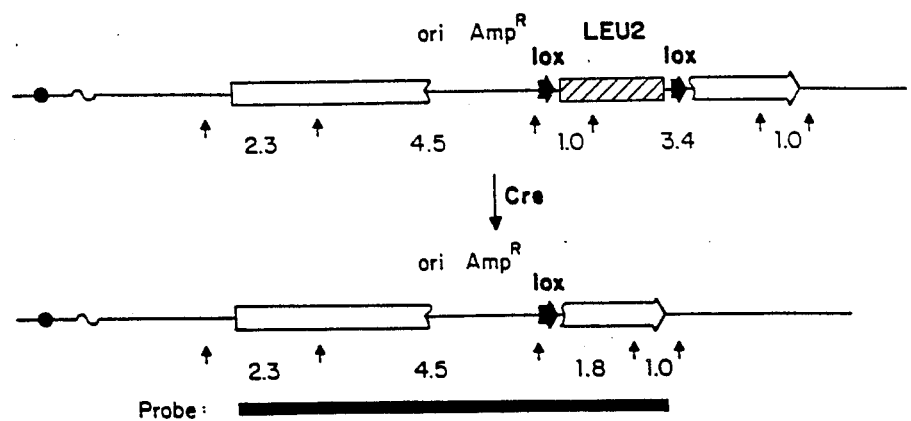

Physical evidence was obtained to demonstrate that the gene product of the cre gene produced recombination at the lox sites located on chromosome 7. Eight independent leucine requiring isolates of yeast strain BSY38 were obtained by plating BSY38 on agar medium containing leucine and galactose. The total DNA from each of these leucine requiring isolates was digested with Eco RI and the structure of the region at which pBS42 had integrated into chromosome 7 was determined by the method of Southern, *J. Mol. Biol.* 98: 503 (1975) using plasmid pBS78 as a probe. Plasmid pBS78 is derived from pBS42 by cre mediated recombination at the lox sites in an *E. coli* stain. Plasmid pBS78 contains sequences homologous to the $Amp^R$ gene of pBR322 and to the segment of chromosome 7 DNA derived from pJM53 but lacks homology with the LEU2 gene of yeast. Homology detected by pBS78 is indicated in FIG. 5 by the solid black bar. FIG. 5 shows the analysis of seven of these leucine requiring derivatives. Shown are the haploid parent DBY931 (lane 1), the haploid BSY4 with the LEU2 containing substrate chromosome 7 (lane 2), the diploid BSY63 which lacks the cre plasmid pBS49 (lane 3), the diploid BSY38 with plasmid pBS49 (lane 4), and seven independent galactose induced leucine requiring derivatives of BSY38 (lanes 5-11). Also shown are the marker plasmids pBS78 and pBS42. The analysis shows that all leucine requiring derivatives lost the 3.4 kb fragment of DNA detected by the probe. Instead, leucine requiring derivatives are shown in FIG. 5 to have a 1.8 kb fragment of DNA as predicted by a deletion of the LEU2 gene. The derivatives all show exactly the same structure indicating deletion had occurred only on the modified chromosome 7 and only at the lox sites. To further show that the specific deletion had occurred, integrated plasmid DNA from each of three of the leucine requiring isolates was recovered by cleaving the genomic DNA with Hind III. The DNA from each isolate was religated and used to transform *E. coli*. The region proximate to the lox site was sequenced for two of the plasmids. The sequences were found to be identical to that predicted by recombination at the lox sites. The third plasmid was found to be identical to the other two by restriction mapping, but no sequencing was conducted.

EXAMPLE 2

Site-Specific Deletion of LEU2 gene in Yeast

The following experiment shows that the recombination event at lox sites in yeast after galactose activation is dependent on a functional cre gene. Plasmid pBS77, a derivative of plasmid pBS49 which contains a non-functional cre gene, was constructed according to the following procedure. Plasmid pBS49 was digested with Bam HI—which cuts within the cre gene—and the resulting staggered ends were made flush using the Klenow fragment of DNA polymerase I. The resulting DNA was religated to form plasmid pBS77 which is identical to pBS49 except that it contains a mutant cre gene which is inactive in *E. coli*. Diploid yeast strains BSY91 and BSY93 were constructed according to the following procedure. Yeast strain DBY745 was transformed with pBS77 and yeast cells able to grow in the absence of uracil were selected. The resulting yeast strain BSY92 was mated with BSY4 to produce BSY93. Similarly, yeast strain DBY745 was also transformed with plasmid pBS39—identical to pBS49 except it lacks the mouse MT-1 DNA sequences—to yield a yeast strain designated BSY90. Yeast strain BSY90 was mated with BSY4 to generate a diploid yeast strain designated BSY91.

The yeast strains shown in Table II were grown on agar medium containing galactose and leucine. Individual colonies were transferred onto agar medium containing glucose and leucine and were then tested for their ability to grow in the absence of leucine by replica plating to appropriate plates. The results are shown in Table II.

TABLE II

| | Deletion of LEU2 Gene | | | |
|---|---|---|---|---|
| Yeast Strain | Plasmid with lox sites | Plasmid with cre gene | Colonies requiring leucine | Total Colonies |
| BSY38 | pBS42 | pBS49 | 10 | 10 |
| BSY91 | pBS42 | pBS39 | 10 | 10 |
| BSY93 | pBS42 | pBS77 | 0 | 10 |
| BSY63 | pBS42 | none | 0 | 10 |

Table II shows that the presene of galactose does not affect deletion of the LEU2 gene in yeast transformed with pBS77 containing the mutant cre gene. Table II also shows that pBS39, which lacks the portion of the mouse metallothionein gene present in pBS49, is capable of expressing the cre gene and affecting recombination at lox sites in yeast DNA. Therefore, no portion of the MT-1 gene is required for expression or function of the cre gene in yeast transformed with plasmid pBS39.

EXAMPLE 3

Site-Specific Deletion of LEU2 Gene in Yeast on Chromosome 13

Figure 6A:
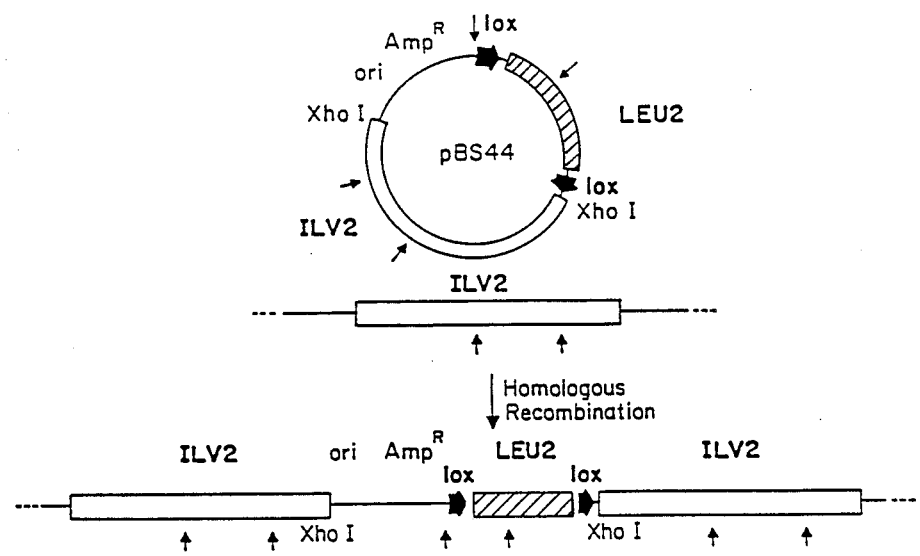
FIG. 6 represents the modification of chromosome 13 of yeast strain DBY931 after homologous recombination with pBS44 (panel A) or pBS47 (panel B), as described in Example 3.
Figure 6B:
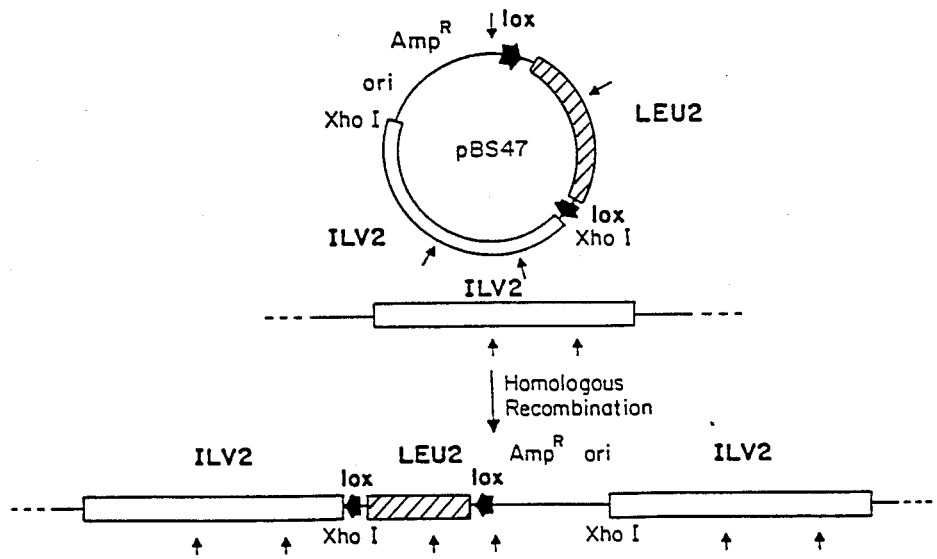

This example demonstrates that Cre mediated recombination at lox sites can occur on a yeast chromosome other than Chromosome 7. Plasmids for inserting a DNA sequence comprising the LEU2 gene flanked by lox sites at the ILV2 locus on chromosome 13 were constructed according to the following method. An allele of ILV2 which codes for sulfometuron methyl resistance is present on plasmid pCP2-4-10 which is disclosed and described by Falco and Dumas, *Genetics* 109: 21 (1985). Plasmid pCP2-4-10 is deposited in the American Type Culture Collection and bears deposit accession number 39606. The Cla I and Hind III sites flanking the ILV2 gene on pCP2-4-10 were converted to Xho I sites. The fragment resulting from digestion with Xho I was inserted into the Xho I site of pBS30 to form plasmids pBS44 and pBS47 which differ only in the orientation of the inserted Xho I fragment containing the ILV2 gene. These two plasmids were integrated into chromosome 13 by transforming yeast strain DBY931 and selecting for non-leucine requiring transformants according to a procedure similar to that described in Example 1. Integration of plasmid pBS44 into the ILV2 locus on chromosome 13 yielded yeast strain BSY23. Integration of plasmid pBS47 into the ILV2 locus resulted in yeast strain BSY27. Non-leucine requiring transformants obtained by transforming yeast cells with pBS44—such as yeast strain BSY23—differ from those obtained by transforming them with pBS47—such as yeast strain BSY27—in that the inserted LEU2 gene has flanking lox sites in opposite orientations with respect to each other, as shown in FIG. 6. The structures of these chromosomes were verified by Southern analysis. Diploid strains of yeast containing one of these chromosomes, and pBS49 which provided a cre gene under control of GAL1 promoter were constructed by (1) mating BSY23 with BSY3 to generate yeast strain BSY31 and also with yeast strain DBY745 to generate the Cre⁻ control yeast strain BSY56, and (2) mating BSY27 with BSY3 to generate yeast strain BSY35 and also with DBY745 to generate the isogenic Cre⁻ control yeast strain BSY59.

The yeast strains shown in Table III were grown on agar medium containing galactose and leucine. Individual colonies were transferred onto agar medium containing glucose and leucine and were then tested for their ability to grow in the absence of leucine by replica plating to appropriate plates. The results are shown in Table III.

TABLE III

| | Deletion of LEU2 Gene | | | |
|---|---|---|---|---|
| Yeast Strain | Plasmid with lox sites | Plasmid with cre gene | Colonies requiring leucine | Total Colonies |
| BSY31 | pBS44 | pBS49 | 5 | 5 |
| BSY56 | pBS44 | none | 0 | 5 |
| BSY35 | pBS47 | pBS49 | 5 | 5 |
| BSY59 | pBS47 | none | 0 | 5 |

Table III shows that transformed strains which contain a cre gene delete the LEU2 gene when grown on galactose containing medium. Thus, the gene product of the cre gene is able to recombine lox sites in either orientation with respect to normal sequence of chromosome 13 to generate chromosomal deletions on chromosome 13 as well as on chromosome 7.

EXAMPLE 4

Site-Specific Inversion of LEU2 Gene in Yeast

Site-specific inversion of LEU2 gene present in yeast DNA is effected according to the following method. A first plasmid containing a cre gene under control of the GAL1 promoter is constructed according to a method similar to that used to construct pBS39 and pBS49 as shown in FIG. 1. A second plasmid containing a selectable marker such as sulfometuron methyl resistance and a LEU2 gene flanked by loxP sites is constructed according to a method similar to that used to construct pBS44 and pBS47 except that the LEU2 gene is inserted into the plasmid (1) without a promoter, (2) with flanking loxP sites in opposite orientations with respect to each other and (3) with 3' end of the LEU2 gene proxmiate to a nucleotide regulatory sequence such that the gene is transcribed in an antisense direction.

A yeast strain which is auxotrophic for leucine is transformed with both plasmids according to a method similar to that described in Example 1 and Example 3. The resulting yeast are grown in a media containing glucose and leucine. The yeast require leucine to grow since the LEU2 gene is inverted with respect to its promoter. The GAL1 promoter is activated by the presence of galactose as described in Example 1 thereby effecting expression of the cre gene and producing the inversion of the LEU2 gene. The resulting yeast are capable of growing in the absence of leucine.

SITE SPECIFIC RECOMBINATIONS IN MAMMALIAN CELLS

Materials and Methods

EXAMPLE 5

Site-Specific Deletion of neo Gene in a Mouse Cell Line

Site-specific deletion of a neo gene from a plasmid DNA molecule present in mouse cell line, C-127, was effected according to the following procedure. The mouse cell line was transformed with plasmid pBS31, containing the cre gene from pBS7 upstream from a MT-1 promoter, to form a stable cell line derivative. Plasmid pRH43, containing two lox sites in the same orientation flanking the neo gene of Tn5, was introduced into the cell line derivative as a transient DNA species. Activation of the MT-1 promoter with $CdCl_2$ effected expression of the cre gene and deletion of the neo gene from pRH43.

Characterization and Construction of pBS31

The construction of plasmid pBS31 was described in Example 1 and is schematically represented in FIG. 1. pBS31 contains the cre gene from pBS7 inserted at the XhoI site of pBMTx. The XhoI site is located between the mouse metallothionein (MT-1) promoter sequence and the MT-1 structural gene plus downstream 3' sequences. The latter sequences contain a polyadenylation signal. The orientation of the cre insertion in the plasmid is such that the 5' end of the cre gene is adjacent to the MT-1 promoter and the 3' end of the cre gene is adjacent to the MT-1 structural gene. From this arrangement, it was predicted that expression of the cre gene should be under the control of the MT-1 promoter, and therefore inducible by heavy metals such as cadmium and zinc as described by Karin et al., Science, 204:176–177 (1978) and Mayo, et al., Cell, 29:99–108 (1982).

pBS31 also contains sequences from bovine papilloma virus (BPV) which allow autonomous replication of the plasmid in mammalian cells as an extrachromosomal element as shown by Law et al., PNAS USA, 78:2727–2731 (1981). The BPV sequences also confer a transformed phenotype which permits the identification of transformed cells as shown by Sarver et al., Mol. Cell. Biol., 1:486–496 (1981).

Transformation of a Mouse Cell Line with pBS31

A confluent layer of mouse cell line, C-127, was transformed with pBS31 by a modification described by Lin et al., Mol. Cell. Biol., 7:129–140 (1987) and IshIura et al., Mol. Cell Biol., 2:607–616 (1982) of the $CaPO_4$ precipitation technique of Graham, F. L. et al., Virology, 52:456–467 (1973). Specifically, a co-precipitate of $CaPO_4$, 50 ng of pBS31 and 10 ug of mouse cell carrier DNA were added to a monolayer culture of C-127 cells which had been prepared the previous day by adding $2.5 \times 10^5$ cells to a 10 cm petri dish. After about 18 hours, the resulting co-precipitate has removed and fresh medium was added. The cells were replated the next day at dilutions of 1/10, 1/50 and 1/100. Thirty days after DNA transformation, individual characteristic foci of cells displaying a transformed phenotype were picked from the transformation plates and cultured in new plates.

A number of transformed cell lines were established after two rounds of selecting characteristically altered colonies from each focus originally picked. DNA was prepared from each of these cell lines and examined by Southern blot analysis to determine whether or not intact cre genes were present in these cells. One of the cell lines, designated strain 55, was found to contain an intact cre gene. DNA was prepared from strain 55 substantially according to the method described by Hirt, *J. Mol. Biol.*, 26:141-144 (1969). This procedure greatly enriches the concentration of lower molecular weight DNA, such as extrachromosomal DNA species, in a purified preparation. Southern analysis of this DNA indicated that (1) pBS31 was present, and (2) it was most likely present as a circular DNA species.

As a control, a second cell line of C-127 cells was transformed with plasmid pBMTx which did not contain a cre gene. This plasmid was the vector from which pBS31 was constructed. The transformation was conducted substantially according to the method described above for preparing strain 55 except for the following modifications. The C-127 cells were transformed with 3 ug of pBMTx DNA and 10 ug of mouse cell carrier DNA. The transformed cells were diluted 1/10, 1/20, 1/50, 1/100 and 1/000 the second day following transformation. At 28 days after transformation, foci were picked and cell lines were established as described above. Southern analysis of DNA from one such cell line, designated 3C-5, showed that it contained pBMTx, most likely as a circular extrachromosomal element. This control showed that the production of black plaques derives from the presence of the cre gene in strain 55 and was not due to the presence of BPV sequences.

Expression of the cre Gene in Mouse Cell Line

Since the cre gene on plasmid pBS31 was placed downstream from the MT-1 gene, it was predicted that the gene's expression was under the control of the MT-1 promoter. This prediction was confirmed by experiments set forth in this section. RNA prepared from strain 55 cells which had been incubated for 4 h with $CdCl_2$ and from untreated cells was tested with a hybridization probe to the cre gene. The following results show that the cre gene was expressed in cell treated with $CdCl_2$ but not in the untreated cells.

Approximately $1.1 \times 10^7$ cells of strain 55 at 50% confluency were incubated with 8 $\mu$M $CdCl_2$ for 4 h. The RNA from these incubated cell was isolated by the guanidine thiocyanate method of Chirgwin et al., *Biochem.*, 18:5294-5299 (1979). The RNA from about $1.7 \times 10^7$ untreated cells of strain 55 was also isolated according to the same procedure. Polyadenylated RNA was recovered from both samples by oligo (dT)-cellulose chromatography as described by Aviv et al., *Proc. Natl. Acad. Sic. USA*, 69:1408-1412 (1972) and Maniatis et al., Molecular Cloning: A Laboratory Manual, Cold Spring Harbor Laboratory, New York (1982).

Equal amounts of polyadenylated RNA (approximately 2.5 ug) from the $CdCl_2$ treated cells and the untreated cells were electrophoresed on a 1.4% agarose gel containing 2.2 M formaldehyde and the resulting samples were subjected to Northern blot analysis with a hybridization probe which contained a copy of the cre gene (Maniatis et al., Molecular Cloning: A Laboratory Manual, Cold Spring Harbor Laboratory, N.Y. (1982)). The probe was the XhoI-SalI DNA fragment of a plasmid pBS1 which had been labelled with $^{32}P$-dCTP by nick translation according to the method of Rigby et al., *J. Mol. Biol.* 113: 327-251 (1977) and the results are shown in FIG. 3-1. It was found that inducing strain 55 with 8 uM $CdCl_2$ for 4 h resulted in a significant stimulation of a cre-specific mRNA molecule which is approximately 2100 nucleotides in length. By quantitating the gel bands on a Hoefer GS300 densitometer, it was calculated that a 60-fold induction of cre-specific mRNA occurred as a result of incubating strain 55 cells with 8 $\mu$M $CdCl_2$ for 4 h.

Activity of cre Gene Product in a Mouse Cell Line

To show that a functional Cre protein was produced in strain 55 cells, the experiment diagrammed in FIG. 3-2 was performed. Plasmid pRH43, which is described by Sternberg et al., *Mechanisms of DNA Replication and Recombination*, pp 671-684, (Alan R. Lis, New York (1983)), contains two directly repeated lox sites flanking the neo gene of Tn5. It was predicted that a cre-mediated recombination at the lox sites of pRH43 would result in the formation of two smaller circular molecules: a 2.3 kb molecule containing the $Amp^R$ gene and a single EcoRI site and a 1.9 kb circular molecule containing the neo gene with a SmaI site, a BglII site, and a BamHI site. This prediction was confirmed by the following experiment.

pRH43 DNA (0.5 $\mu$g per culture) was introduced into six cell cultures substantially according to the $CaPO_4$-mediated DNA transformation procedure described above After about 14 hours, fresh medium was placed on the transformed cells. The first and fourth cultures consisted of transformed C-127 cells and strain 55 cells, respectively, which were not treated with $CdCl_2$ (lanes 1 and 4 of FIG. 7). The second and fifth cultures consisted of transformed C-127 cells and strain 55 cells, respectively, each of which had been incubated for 5 h with medium and then incubated with 8 uM $CdCl_2$ for 4 hours. The $CdCl_2$ was removed and replaced with fresh medium and the resulting cultures were incubated for an additional 21 hour expression period (lanes 2 and 5 of FIG. 7). The third and sixth cultures consisted of transformed C-127 cells and strain 55 cells, respectively, each of which had been incubated and for 24 h with medium and then incubated with 20 mM $CdCl_2$ for 4 hours. The $CdCl_2$ was removed and replaced with fresh medium and the resulting cultures were incubated for an additional 2 hour expression period (lanes 3 and 6 of FIG. 7).

Figure 7:
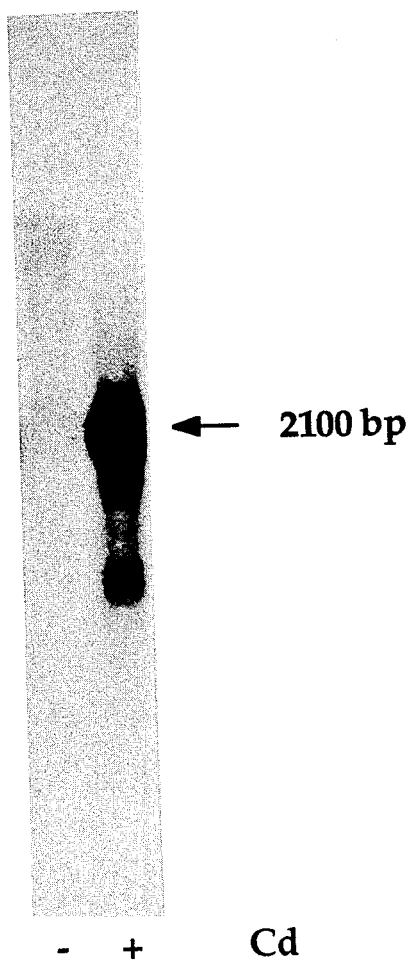
FIG. 7 shows an agarose gel prepared from polyadenylated RNA isolated from a mouse cell line containing a cre gene under the control of the MT-1 promoter. The RNA is lane 1 was prepared from uninduced cells and the RNA in lane 2 was prepared from cells induced with $CdCl_2$.
Figure 8:
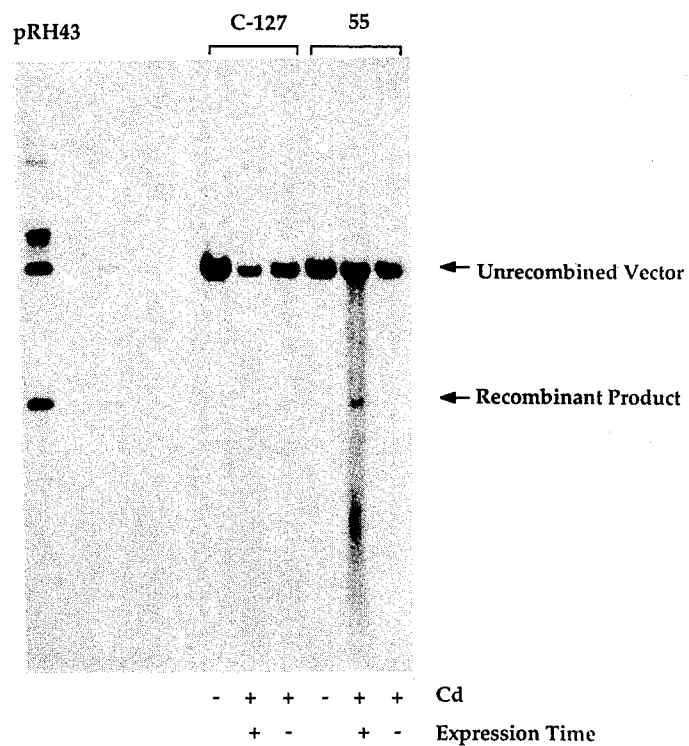
FIG. 8 shows a Southern blot analysis of DNA preparations obtained from untreated mouse cells, mouse cells subjected to $CaPO_4$ transfer of pRH43 DNA, and Cre reacted plasmid pRH43 as described in Example 5. The DNA's were hybridized with a $^{32}P$ labeled neo-specific DNA probe. The positions of BglII linearized pRH43 fragment and of the 1.9 kb linearized BglII fragment containing the neo gene obtained after recombination are indicated. For the untreated cells and those containing pRH43, lane 1 was prepared from uninduced cells, lane 2 was prepared from cells which had been induced for 4 hours with 8 uM $CdCl_2$ and allowed to recover for 21 hours (expression time), and lane 3 was prepared from cells induced for 4 h with 20 uM $CdCl_2$ and allowed to recover for only 2 hours.

DNA was prepared from the second and fifth cultures after each culture had experienced the 21 hour expression period described above and from the third and sixth cultures after each culture had experienced the 2 hour expression period described above DNA was also prepared from first and third cultures which had not been treated with $CdCl_2$. Equal amounts of DNA from each culture was digested with BglII and the resulting fragments were electrophoresed on a 0.8% agarose gel and subjected to Southern analysis using a $^{32}P$-labeled neo specific DNA probe. The results are shown in FIG. 7.

BglII digestion of pRH43 produced a 4.2 kb unrecombined linear fragment of DNA containing the neo gene. Linear pRH43 DNA was incubated with Cre in vitro to generate the 1.9 kb DNA fragment containing the neo gene which results when Cre recombination occurs at the lox sites of pRH43 (labeled pRH43 at the top in FIG. 7). This recombination event did not occur in C-127 cells even if they were induced with $CdCl_2$ (the three lanes under label C-127 in FIG. 7). However, in 55 cells which were induced with $CdCl_2$ and then allowed to express the cre gene for 21 hours, recombination at the lox sites had taken place to form the 1.9 kb recombinant DNA molecule (middle lane under label 55 in FIG. 7). Little or no recombination occurred in either uninduced 55 cells or in 55 cells induced 45 h after the introduction of pRH43 DNA but allowed only a 2 h expression time prior to DNA collection.

These results show that the cre gene in strain 55 cells was under the control of the mouse metallothionein MT-1 promoter. The results further show that (1) Cre protein was produced when the promoter was induced by CdCl₂, (2) the Cre produced was functional, and (3) the Cre protein was able to produce site specific DNA recombinations at lox sites within mammalian cells.

EXAMPLE 6

Reconstruction of Disrupted gIII gene by Site Specific Recombination

Strain 55 cells were infected with PRV42::pBS64 virus, a recombinant pseudorabies virus which contains a gIII gene disrupted by two lox sites connected by heterologous DNA from pBS64. Expression of Cre protein produced site specific recombinations which resulted in the reconstruction of the gIII gene. This event was detected by a black plaque assay.

Construction of the PRV42::pBS64 Virus and the Black Plaque Assay.

Cre mediated recombination was carried out between the loxC2 site on the linear PRV42 genome and the loxP site or the small circular plasmid, pBS64, as shown in FIG. 4-1, in vitro. This recombination event resulted in the integration of the circular plasmid into the PRV genome to generate PRV42::pBS64. Virus, containing the inserted DNA fragment, was recovered by transfecting DNA from the recombination experiments into PK15 cells, a porcine kidney cell line which is the usual host for pseudorabies virus. Both infective centers and progeny virus were screened by the black plaque assay.

The black plaque assay employed to detect virus which had an altered gIII protein was conducted substantially according to the procedure described by Robbins, et al., *J. Virol.*, 58:339-347 (1986), Holland, et al., *J. Virol.*, 46:649-652 (1983) and Smith, et al., *J. Immunol. Methods*, 40:297-305 (1981). This technique uses the M1 monoclonal antibody to gIII, described by Hampl, et al., *J. Virol.*, 52:566-574 (1984), and a horseradish peroxidase linked second antibody to detect the M1 antigen. M1 monoclonal antibody used in the examples was a gift of Dr. Tamar Ben-Porat, Vanderbilt University. PRV42 contains a gIII-lox fusion gene which contains a lox site inserted at the KpnI site of gIII. Even though PRV42 contains the specified insertion, this virus displays an intact M1 epitope which makes a black plaque when reacted with a gIII M1 monoclonal antibody. An important feature of PRV42::pBS64 DNA is that it contains a 3.1 kb insertion at the PRV gIII gene at the Kpn1 site which abolishes the epitope recognized by the gIII M1 monoclonal antibody. As a result, PRV42::pBS64 virus produces a white plaque in the assay.

It was found that incubation of PRV42::pBS64 DNA with Cre protein in vitro resulted in the regeneration of PRV42 and pBS64. The PRV42 virus so regenerated was detectable by the black plaque assay. It was predicted that if strain 55 cells produced a functional Cre protein then infection of strain 55 with PRV42::pBS64 virus should result in the generation of black plaque forming PRV42. Such black plaque forming viruses would only be formed by the precise recombination of the two directly repeated lox sites of PRV42::pBS64 DNA to generate an open reading frame allowing the production of a gIII protein which exhibits the M1 epitope, as diagrammed in FIG. 4-1. This prediction was confirmed in the following experiment.

Infection of a Mouse Cell Line with PRV42::pBS64 Virus

Strain 55 cells which contained the cre gene (Cre +) and C-127 cells which did not contain the cre gene (Cre−), were infected with PRV42::pBS64 virus on plates to allow plaque formation. Two days after infection, the resulting plaques were stained with the M1 monoclonal antibody using the black plaque procedure. The results, are presented in Table 4-1.

TABLE 4-1

| | Plaque Type | |
| Cells | Black | White |
| --- | --- | --- |
| C-127 (Cre−) | 0 | 765 |
| 55 (Cre+) | 135 | 361 |
| 3C-5 (Cre−) | 0 | 351 |
| PK15 (Cre−) | 0 | 2450 |

About 25% of the plaques formed on strain 55 were not white but instead show a black and white sectored phenotype, implying that a subpopulation of virus in these plaques has undergone recombination to regenerate the M1 epitope. Plaques formed on the parental C-127 cell line were all white, implying that no recombination has taken place. As additional controls PRV42::pBS64 virus was plated on PK15 cells and on cells of the mouse cell line 3C-5 which was derived from C-127 by transforming it with pBMTx, the plasmid which served as the parent to the Cre vector pBS31. In both cases only white plaques were observed.

The sectored plaques suggest that recombinant (black-plaque-forming) virus is present after growth in strain 55 cells. PRV42::pBS64 viral stocks were prepared on both C-127 and strain 55 cells. Because Cre production in strain 55, is stimulated by inducing the cells with CdCl₂, viral stocks were also prepared on C-127 and strain 55 cells which had been incubated (induced) with 2 uM CdCl₂. The resulting viral stocks were then plated on PK15 cells and the resulting plaques were analyzed by the black plaque assay.

Monolayer cell cultures in 10 cm plate of cells at 70-90% confluency were infected with 1.5×10⁵ pfu/plate of PRV42::pBS64 virus. Strain 55 cells which had been incubated with CdCl₂ had 2 uM CdCl₂ added to the medium 5 h before infection. The cells were washed with PBS before infection to remove CdCl₂ Viral stocks were harvested 34 h after infection, then plated on PK15 cells and the plaques stained using the M1 antibody in the black plaque assay. The results are presented in Table 4-2.

TABLE 4-2

| | | Plaque Type | |
| Cells | Cd Induction | Black | White |
| --- | --- | --- | --- |
| C-127 | no | 0 | 2106 |
| C-127 | yes | 0 | 1500 |
| 55 | no | 22 | 641 |
| 55 | yes | 11 | 519 |

Black plaque-forming viruses were generated when PRV42::pBS64 viruses replicate in strain 55 cells either in the presence or absence of CdCl₂ induction. These viruses represented about 2-3% of the viral stock. Of 2106 plaques examined from a virus stock prepared on the uninduced parental C-127 cell line, no black plaques were observed. Similarly of 1500 plaques examined from a viral stock prepared on C-127 cells which had been incubated with CdCl₂, no black plaques were observed. Thus, black plaque-forming recombinant viruses were produced only after infection of the cell line containing the cre gene.

EXAMPLE 7

Reconstruction of Disrupted gIII gene by Site Specific Recombination

The experiment described in Example 6 was substantially repeated with strain 55 cells except for the following changes. Strain 55 cells incubated with 2 uM CdCl₂ were induced for 11.5 h and viral stocks were harvested 62.5 hour after infection. The results are shown in Table 4-3.

TABLE 4-3

| Cells | Cd Induction | Plaque Type Black | White |
|---|---|---|---|
| 55 | no | 56 | 194 |
| 55 | yes | 76 | 400 |

Again viral stocks prepared on strain 55 cells contain a high proportion of black plaque-forming recombinant viruses, as high as 22%. Thus, a functional Cre protein is expressed in these cells and is able to cause site specific recombination on an infecting viral genome.

What is claimed is:

1. A method for producing site-specific recombination of DNA in eukaryotic cells, comprising,
   (a) introducing into the cells a first DNA sequence comprising a first lox site and a second DNA sequence comprising a second lox site, and
   (b) contacting the lox sites with Cre, thereby producing the site specific recombination.

2. A method as defined in claim 1, wherein a third DNA sequence comprising a cre gene is also introduced into the cells.

3. A method as defined in claim 2, wherein the third DNA sequence further comprises a regulatory nucleotide sequence and expression of the cre gene is produced by activating the regulatory nucleotide sequence.

4. A method as defined in claim 3, wherein the first and second DNA sequences are introduced into the cells connected by a pre-selected DNA segment.

5. A method as defined in claim 4, wherein the first and second lox sites have the same orientation and the site specific recombination of DNA is a deletion of the pre-selected DNA segment.

6. A method as defined in claim 5, wherein the cre gene is isolated from bacteriophage P1.

7. A method as defined in claim 5, wherein the first and second lox sites are loxP or loxC2.

8. A method as defined in claim 7, wherein the preselected DNA segment is a gene for a structural protein, an enzyme, or a regulatory molecule.

9. A method as defined in claim 8, wherein the eukaryotic cell is a mammalian cell.

10. A method as defined in claim 8, wherein the eukaryotic cell is yeast.

11. A method as defined in claim 4, wherein the first and second lox sites have opposite orientations and the site-specific recombination is an inversion of the nucleotide sequence of the pre-selected DNA segment.

12. A method as defined in claim 11, wherein the cre gene is isolated from bacteriophage P1.

13. A method as defined in claim 12, wherein the first and second lox sites are loxP or loxC2.

14. A method as defined in claim 13, wherein the pre-selected DNA segment is a gene for a structural protein, an enzyme, or a regulatory molecule.

15. A method as defined in claim 1, wherein the second and third DNA sequences are introduced into two different DNA molecules and the site-specific recombination is a reciprocal exchange of DNA segments proximate to the lox sites.

16. A method as defined in claim 15, wherein the cre gene is isolated from bacteriophage P1.

17. A method as defined in claim 16, wherein the first and second lox sites are loxP and loxC2.

18. A eukaryotic cell transformed with a DNA sequence comprising a cre gene.

19. A eukaryotic cell transformed with a DNA sequence comprising a lox site.

20. A method for producing site-specific recombination of DNA in yeast, comprising:
   (a) introducing into the DNA the following DNA sequences:
      (i) a DNA sequence comprising a regulatory nucleotide sequence and a cre gene,
      (ii) a DNA sequence comprising a first lox site, and
      (iii) a DNA sequence comprising a second lox site, and
   (b) activating the regulatory nucleotide sequence thereby effecting expression of the cre gene and producing the site-specific recombination.

21. A method as defined in claim 1, wherein the DNA sequences comprising lox sites are introduced into the DNA in yeast connected by a pre-selected DNA segment.

22. A method as defined in claim 21, wherein the cre gene is isolated from bacteriophage P1.

23. A method as defined in claim 22, wherein the first and second lox sites are loxP or loxC2.

24. A strain of yeast transformed with the following DNA sequences:
   (i) a DNA sequence comprising a regulatory nucleotide sequence and a cre gene,
   (ii) a DNA sequence comprising a first lox site, and
   (iii) a DNA sequence comprising a second lox site.

25. A strain of yeast as defined in claim 24, wherein the DNA sequences comprising lox sites are connected by a pre-selected DNA segment.

26. A strain of yeast as defined in claim 25, wherein the cre gene is isolated from bacteriophage P1.

27. A strain of yeast as defined in claim 26, wherein the first and second lox sites are loxP or loxC2.

28. Yeast strain BSY90 having deposit accession number ATCC 20772.

29. Yeast strain pBSY23 having deposit accession number ATCC 20773.

30. A plasmid having a regulatory nucleotide sequence and a cre gene, said plasmid being capable of transforming a eukaryotic cell.

31. A plasmid as defined in claim 30, wherein the cre gene is isolated from bacteriophage P1.

32. A plasmid as defined in claim 30, wherein the plasmid is pBS39 characterized by the restriction enzyme map shown in FIG. 1.

33. A plasmid as defined in claim 30, wherein the plasmid is pBS49 characterized by the restriction enzyme map shown in FIG. 1.

34. A plasmid having at least one lox site, said plasmid being capable of transforming a eukaryotic cell.

35. A plasmid as defined in claim 34, wherein a first lox site and a second lox site are connected by a pre-selected DNA segment.

36. A plasmid as defined in claim 35, wherein the first and second lox sites are LoxP sites.

37. A plasmid as defined in claim 34, wherein the plasmid is pBS44 characterized by the restriction enzyme map shown in FIG. 6, or a derivative thereof carrying a pre-selected DNA segment other than or in addition to the LEU2 gene and located between the first and second lox sites.

38. A plasmid as defined in claim 34 wherein the plasmid is pBS47 characterized by the restriction enzyme map shown in FIG. 6, or a derivative thereof carrying a pre-selected DNA segment other than or in addition to the LEU2 gene and located between the first and second lox sites.

39. A plasmid as defined in claim 34 wherein the plasmid is pBS42 characterized by the restriction enzyme map shown in FIG. 2, or a derivative thereof carrying a pre-selected DNA segment other than or in addition to the LEU2 gene and located between the first and second lox site.

40. A plasmid as defined in claim 34 wherein the plasmid s pBS43 characterized by the restriction enzyme map shown in FIG. 2, or a derivative thereof carrying a pre-selected DNA segment other than or in addition to the LEU2 gene and located between the first and second lox sites.

* * * * *